(12) United States Patent
King et al.

(10) Patent No.: US 9,937,445 B2
(45) Date of Patent: Apr. 10, 2018

(54) SYSTEM AND METHOD FOR SEPARATING A FRACTION

(71) Applicant: Biomet Biologics, LLC, Warsaw, IN (US)

(72) Inventors: William King, Warsaw, IN (US); Jennifer E. Woodell-May, Warsaw, IN (US); Joel C. Higgins, Claypool, IN (US); Michael D. Leach, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 390 days.

(21) Appl. No.: 14/269,655

(22) Filed: May 5, 2014

(65) Prior Publication Data
US 2015/0273360 A1    Oct. 1, 2015

Related U.S. Application Data

(60) Provisional application No. 61/971,261, filed on Mar. 27, 2014.

(51) Int. Cl.
*B01D 21/00* (2006.01)
*A61M 1/36* (2006.01)
(Continued)

(52) U.S. Cl.
CPC ........... *B01D 21/003* (2013.01); *A61M 1/029* (2013.01); *A61M 1/3693* (2013.01);
(Continued)

(58) Field of Classification Search
CPC ............ B01D 21/003; B01D 2275/302; B01D 21/307; B01D 21/262; B01D 2221/10;
(Continued)

(56) References Cited

U.S. PATENT DOCUMENTS 1,647,809 A * 11/1927 Neumann ............... B01D 35/05
                                                        210/242.1
2,921,969 A *  1/1960 Loy ...................... B01D 9/0009
                                                        210/187
(Continued)

FOREIGN PATENT DOCUMENTS

CN         1321103 A    11/2001
CN         1322146 A    11/2001
(Continued)

OTHER PUBLICATIONS

Chinese Office Action dated Nov. 21, 2014 for Chinese Patent Application No. 201280030026.X.
(Continued)

*Primary Examiner* — David C Mellon
*Assistant Examiner* — Liam Royce
(74) *Attorney, Agent, or Firm* — Schwegman Lundberg & Woessner, P.A.

(57) ABSTRACT

A material separation system and method is disclosed. The system may include a buoy having a volume that includes or houses a reacting component. The buoy may be placed in a container to hold the material to be separated during a separation procedure. The separated material may be used to various procedures following separation.

13 Claims, 8 Drawing Sheets

(51) Int. Cl.
  *B01D 17/02* (2006.01)
  *G01N 33/49* (2006.01)
  *A61M 1/02* (2006.01)
  *B01L 3/00* (2006.01)
  *B01D 21/30* (2006.01)
  *B01D 21/26* (2006.01)

(52) U.S. Cl.
  CPC ....... *A61M 1/3695* (2014.02); *B01D 17/0217* (2013.01); *B01D 21/262* (2013.01); *B01D 21/307* (2013.01); *B01L 3/50215* (2013.01); *G01N 33/491* (2013.01); *B01D 2221/10* (2013.01); *B01L 2400/0409* (2013.01); *B01L 2400/0633* (2013.01)

(58) Field of Classification Search
  CPC ............................ B01D 2201/64; B01D 35/05; B01D 17/0217; G01N 33/491; A61M 1/029; A61M 1/3695; A61M 1/3693; B01L 2400/0633; B01L 3/502–3/50215; B01L 2400/0409
  See application file for complete search history.

(56) References Cited

U.S. PATENT DOCUMENTS

| | | | |
|---|---|---|---|
| 3,957,554 A | | 5/1976 | Sundin |
| 3,957,654 A | * | 5/1976 | Ayres .................. G01N 33/491 210/516 |
| 5,358,644 A | * | 10/1994 | Dennis ............... B01D 21/2444 137/398 |
| 8,783,470 B2 | | 7/2014 | Hecker et al. |
| 8,801,586 B2 | | 8/2014 | Dorian et al. |
| 8,808,551 B2 | | 8/2014 | Leach et al. |
| 8,950,586 B2 | | 2/2015 | Dorian et al. |
| 8,992,862 B2 | | 3/2015 | Leach et al. |
| 9,011,800 B2 | | 4/2015 | Leach et al. |
| 2002/0090741 A1 | * | 7/2002 | Jurgensen ........... B01L 3/50215 436/523 |
| 2013/0068676 A1 | * | 3/2013 | Leach .................. A61M 1/029 210/123 |
| 2013/0116103 A1 | * | 5/2013 | Lundt ................ B01L 3/50215 494/37 |
| 2013/0259951 A1 | | 10/2013 | O'Connell |
| 2014/0262669 A1 | * | 9/2014 | Conti ........................ F16D 7/02 192/56.61 |
| 2014/0275497 A1 | | 9/2014 | Leach et al. |
| 2014/0349388 A1 | | 11/2014 | Dorian et al. |
| 2014/0356446 A1 | | 12/2014 | Leach et al. |

FOREIGN PATENT DOCUMENTS

| | | |
|---|---|---|
| FR | 2338084 A1 | 8/1977 |
| JP | 2000-189407 A | 7/2000 |
| JP | 2005013783 A | 1/2005 |
| JP | 2009-155234 A | 7/2009 |
| WO | WO-2015148744 A1 | 10/2015 |

OTHER PUBLICATIONS

International Preliminary Report on Patentability and Written Opinion dated Mar. 12, 2015 for PCT/US2013/056793 claiming benefit of U.S. Appl. No. 13/595,461, filed Aug. 27, 2012.
Preliminary Notice of Reasons for Rejection for Japanese Patent Application No. 2014-024420 dated Feb. 24, 2015.
"International Application Serial No. PCT/US2015/022619, International Search Report dated Jun. 25, 2015", 4 pgs.
"International Application Serial No. PCT/US2015/022619, Written Opinion dated Jun. 25, 2015", 7 pgs.
Japanese Office Action dated Sep. 9, 2014 for Japan Patent Application No. 2012-520742,which claims benefit of PCT/US2010/041942 filed Jul. 14, 2010, which claims benefit of U.S. Appl. No. 12/504,413, filed Jul. 16, 2009.
Chinese Office Action dated Jun. 30, 2014 for Chinese Patent Application No. 201080019707.7, which claims benefit of PCT/US2010/029957 filed Apr. 5, 2010, which claims benefit of U.S. Appl. No. 12/417,789, filed Apr. 3, 2009.
Minivalve international: duckbill valves—du 054.001 sd, <http://www.minivalve.com/htm/DV054.htm>, Accessed Jun. 30, 2014, 1 page.
Momentive Silopren*LSR 2050, Jun. 30, 2014, 3 pages.
Vernay Product Information Sheet, Umbrella Check Valve, Part No. V251010200, Jul. 2013, 2 pages.
"Application Serial No. 15717323.8, Response filed May 18, 2017 to Action dated Nov. 11, 2016", 16 pgs.

* cited by examiner

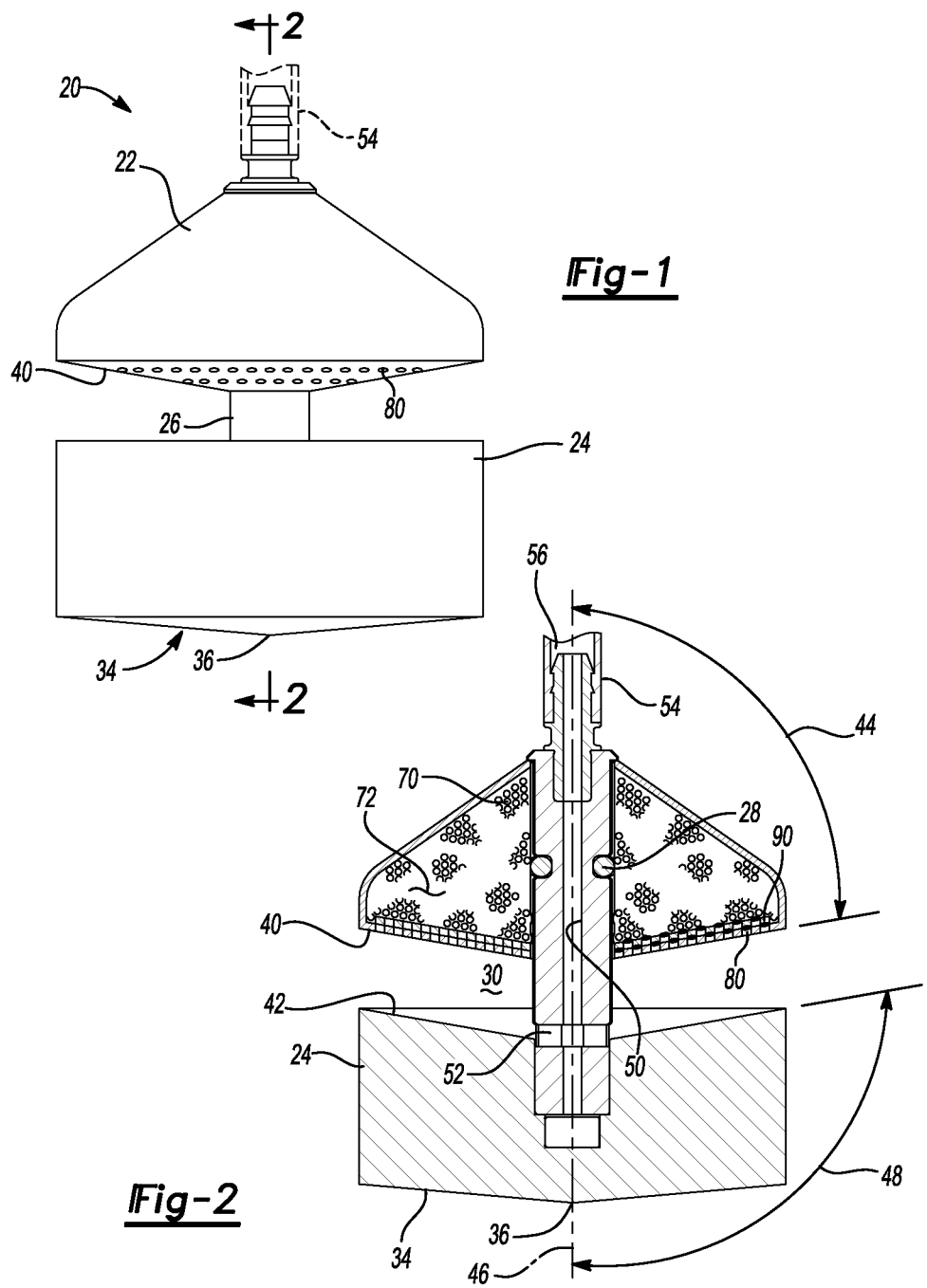

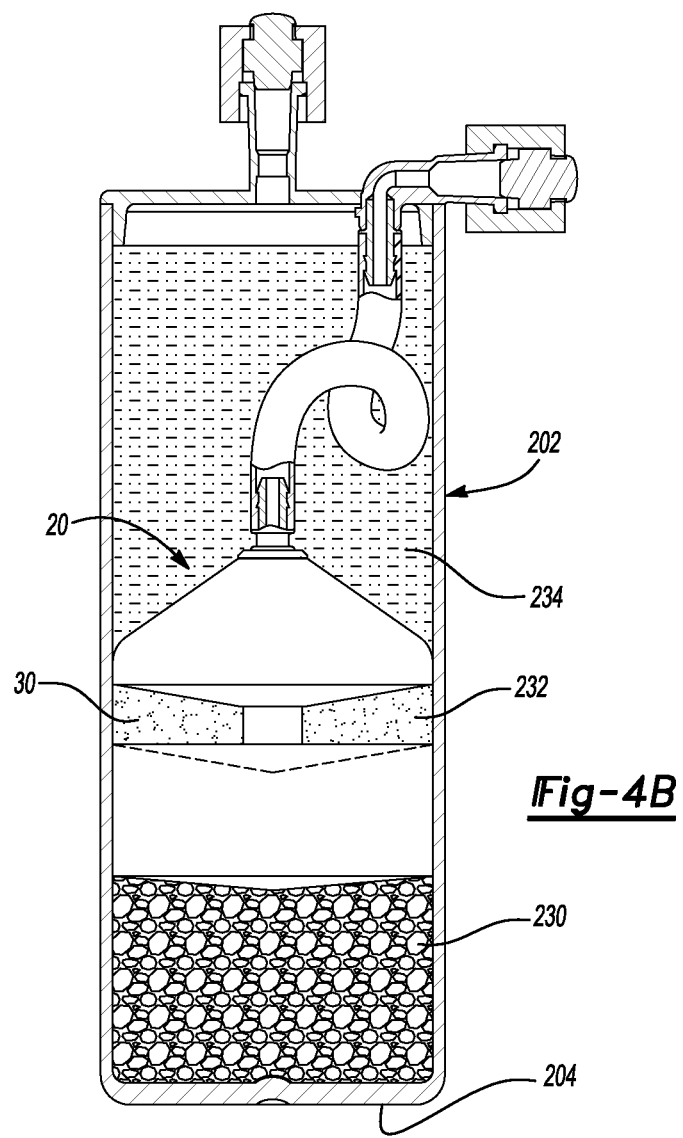

US 9,937,445 B2

SYSTEM AND METHOD FOR SEPARATING A FRACTION

FIELD

The subject disclosure relates to a system for separating materials, and particularly to a buoy system for separating a component from a multiple component material.

BACKGROUND

This section provides background information related to the present disclosure which is not necessarily prior art.

A multiple component material, such as whole blood, plasma, bone marrow aspirate, other suspensions, such as environmental water samples, mercury samples, and the like, may be selected to be separated. Various systems can be used to separate the whole material, such as a centrifuge system. A centrifuge system centrifuges a whole sample to cause a separation of the sample based upon densities and specific densities of materials within the whole material. For example, a centrifuge can be used to separate red blood cells from a whole blood sample.

SUMMARY

This section provides a general summary of the disclosure, and is not a comprehensive disclosure of its full scope or all of its features.

A centrifuge system can be used to separate a selected component of a whole or multiple component sample, such as separating a selected portion of whole blood or separating a reaction product from a sample. According to various embodiments, a buoy system can be positioned within a separation container to assist in separation. For example, a buoy can be provided with a specific density that is equivalent to a selected component within a mixture such that the buoy will move to a position adjacent to the selected component to assist in separating and maintaining a separation of the selected component. The buoy may also include a plurality of portions such that the buoy may sequester a specific area between a first buoy portion and second buoy portion.

Further, the buoy may include a volume that includes or houses a reacting component, such as glass beads, desiccating beads, a reagent, or the like. According to various embodiments, the buoy can include a first buoy member or portion that has a substantially hollow interior to house the reacting component, such as glass beads, and an opening that allows for selective entry of the selected component to interact with the beads housed within the buoy member.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a side plan view of a buoy system according to various embodiments;

FIG. 2 is a cross-section view of the buoy system of FIG. 1 along line 2-2;

Figure 3A:
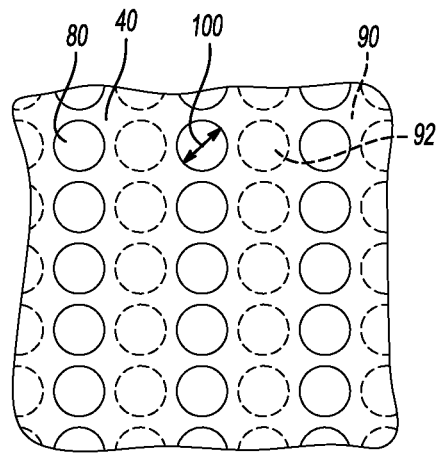
Figure 3B:
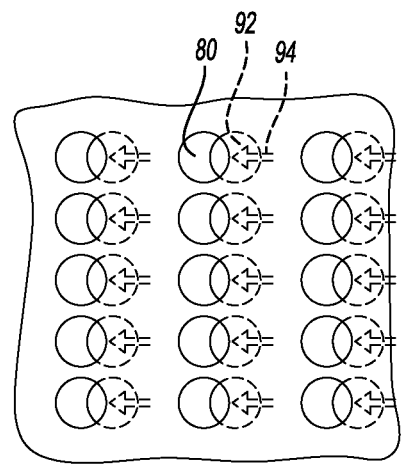
Figure 3C:
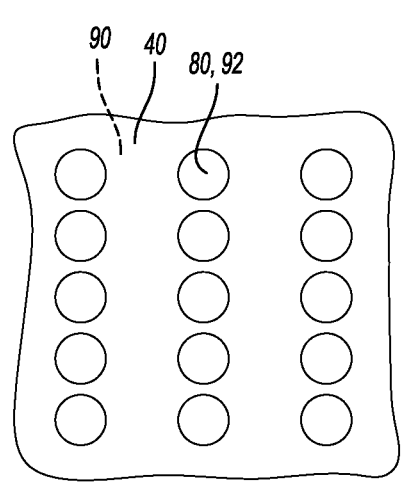
Figure 5A:
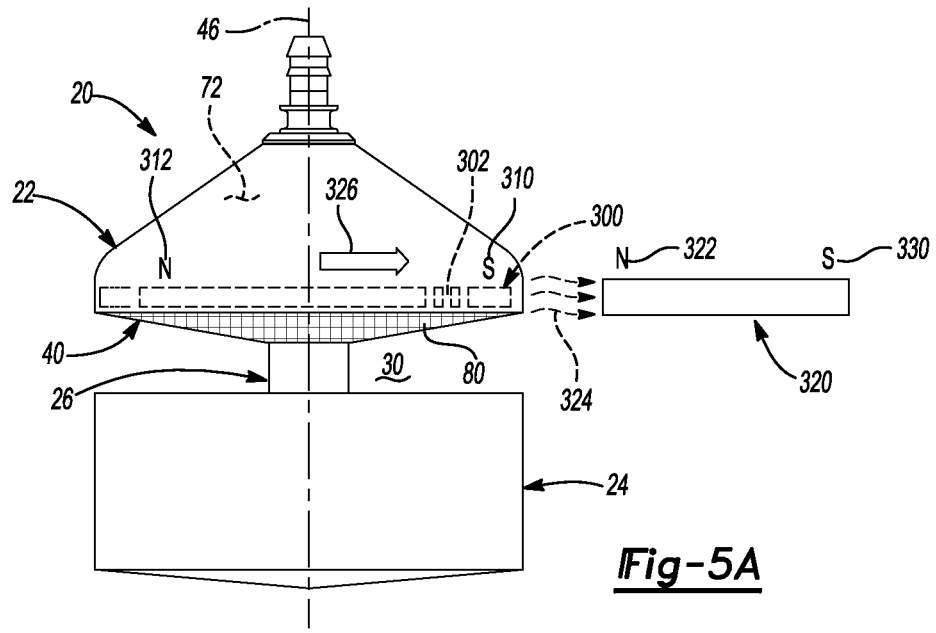
Figure 5B:
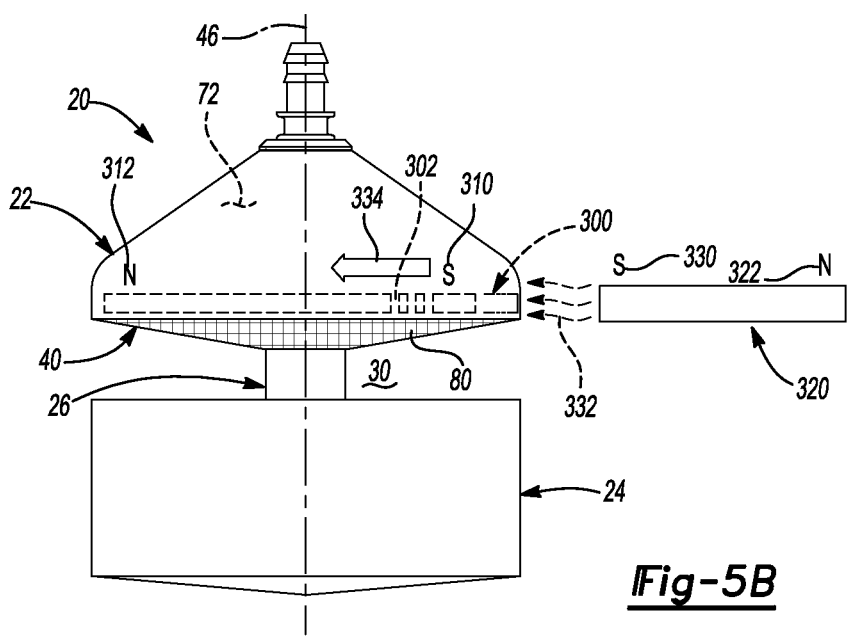

FIG. 3A-3C schematically illustrate movement and/or alignment of a portion of the buoy system;

FIGS. 4A-4E illustrate an exemplary method of use of a system including the buoy system, according to various embodiments;

FIG. 5A is a side plan view of a buoy system with a blocking wall in a first position, according to various embodiments; and FIG. 5B is a side plan view of a buoy system with a blocking wall in a second position, according to various embodiments.

Corresponding reference numerals indicate corresponding parts throughout the several views of the drawings.

DETAILED DESCRIPTION

Example embodiments will now be described more fully with reference to the accompanying drawings.

With reference to FIGS. 1 and 2, a buoy system 20 is illustrated. The buoy system 20 can include portions that are similar to buoy systems included or disclosed in U.S. Pat. Nos. 7,179,391; 7,374,678; 7,832,566; 7,845,499; or 8,567,609; all of which are incorporated herein by reference; and in various devices, such as the PLATELET SEPARATE SYSTEM GPS II® sold by Biomet, Inc. having a place of business in Warsaw, Ind. Generally, the buoy system 20 can include a first or upper buoy member 22 and a lower or second buoy member 24 that can be interconnected with a third buoy portion or member 26. According to various embodiments, the first buoy member 22 can move relative to the second buoy member 24 such as by moving or sliding axially along the third buoy member 26 generally towards the second buoy member 24. If the first buoy member 22 is provided to move relative to the second buoy member 24 a seal, such as a rubber or rubberized O-ring 28 can be provided to assist in providing a seal between an area or volume, such as a collection volume 30. between the first buoy member 22 and the second buoy member 24 and the volume outside of the collection volume 30, such as above the first buoy member 22 and below the second buoy member 24.

Further, according to various embodiments, the second buoy member 24 can be provided of a single or multiple materials in single or multiple sections. Multiple sections may all be made of the same material as well. Further, the second buoy member 24 can be substantially solid. The second buoy member 24 can include a density or specific gravity, as discussed further herein, that in combination with the other portions of the buoy system 20 can be formed to reach a selected region or section within a separation container, as discussed further herein. Further, the second buoy member can include a non-flat or non-planar bottom surface 34, such that the bottom surface 34 may include an apex or point 36 that can assist with initial movement of the buoy member or assembly 20 during the separation, again as discussed further herein.

The buoy assembly 20 can include the collection area 30 that is bounded at least on two sides by the buoy assembly 20. On a first side, a bottom wall 40 of the first buoy 22 can be formed and extend from the third buoy member 26 to an edge of the first buoy member 22. On a second side, a second wall 42, formed as a top surface of the second buoy 24 may extend out from the third member 26 to an edge of the second buoy member 24. The first wall 40 may extend at an angle 44 from a central or long axis 46 of the buoy assembly 20. The second wall 42 can extend at an angle 48 relative to the long axis 46. The angles 44 and 48 may be substantially complimentary such that the first wall 40 may mate with the second wall 42 if the first buoy member 22 is configured to move relative to the second buoy member 24. As illustrated, the first wall 40 may be convex and the second wall 42 may be concave. Accordingly, the collection area 30 can be substantially closed or eliminated by the contact of the first wall 40 with the second wall 42, such as during withdrawal of a material from the collection volume 30.

The third buoy member 26 may have central bore 50 that can extend to terminate in an access bore or extending bore 52. Accordingly, material that is collected within the collection of volume 30 can be withdrawn through the collection bore 52 and the central bore 50 through a collection tube or assembly 54, as discussed further herein. The central bore 50 can be in communication with a bore or passage 56 of the collection tube 54 to assist in withdrawal of material from the collection volume 30.

The first buoy 22 and/or the second buoy member 24 can house a selected material such as glass beads, desiccating beads, a reagent, or other selected material. As exemplarily illustrated in FIG. 2, a desiccating bead 70 or a plurality of desiccating beads 70 can be contained within a containment volume 72 of the first buoy 22. The containment volume 72 can be formed to be an entire volume within the first buoy 22 or any selected portion of the volume within the first buoy 22. The first wall 40 may define a plurality of passages 80 through the wall 40 such that a material within the collection area 30 can move into the volume 72 of the first buoy member 22.

With reference to FIG. 3A and continuing reference to FIGS. 1 and 2, the first wall 40 including the passages 80 can also include a wall or blocking member 90 that may have one or more complimentary or equivalent passages 92. The blocking wall 90 in a first position, as illustrated in FIG. 3A, has the passages 80 through the first wall 40 completely blocked by the blocking wall 90 due to the offset or displacement of the blocking wall passages 92 from the passages 80. In a selected embodiment, as discussed further herein, the blocking wall 90 can be moved to a second position, such as in the direction of arrows 94 such that the blocking wall passages 92 can be aligned in the second position with the passages 80 in the first wall 40, as illustrated in FIG. 3b. With reference to FIG. 3C, the passages 80 and the blocking wall passages 92 can be aligned such that material can generally freely move from the collection reservoir 30 into the volume 72 of the first buoy member 22.

As illustrated in FIG. 3C, when the passage 80 in the first wall is aligned with the blocking wall passage 92 in the blocking wall 90 in the second position, an open passage from the collection area 30 into the volume 72 of the first buoy 22 is made. The blocking wall 90, therefore, can be manipulated to either open or close the wall passages 80 through the first wall 40 to allow material to move into the volume 72 of the first buoy member 22. The blocking wall 90 can also be moved to block or hold the material within the volume 72 of the first buoy member 22 by manipulating the blocking wall 90. In various embodiments, the blocking wall 90 may move in a track or groove that is formed on or in the buoy member 22.

The passages 80 can have a selected diameter or dimension, such as diameter 100 that is sized to ensure that the beads 70 are maintained within the volume 72 even when the passages 80 are in the open configuration, as illustrated in FIG. 3C. Accordingly, a diameter 100 can be equal to, smaller than, or at a dimension selected such that a plurality of the beads will not pass through the passages 80 in the open configuration. For example, the dimension 100 can be about 5 micrometers (μm) to about 1 mm.

Figure 4A:
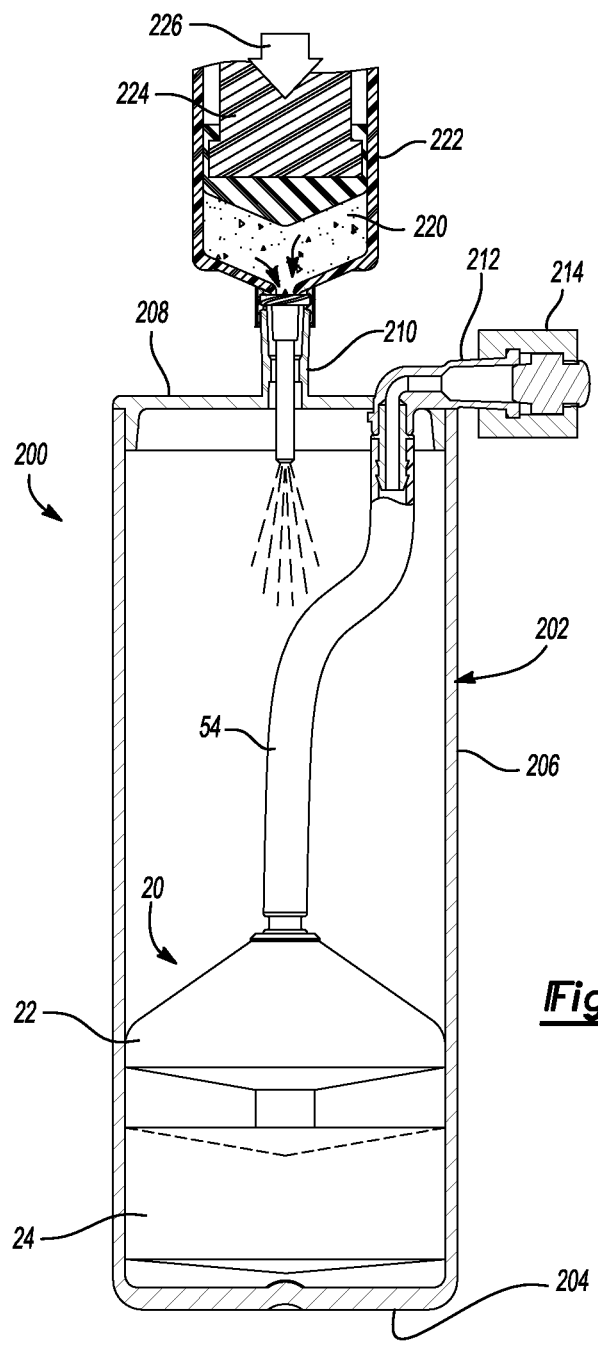

Turning to FIGS. 4A-4E, the buoy assembly 20 can be implemented in a separation and collection system 200. The collection system 200 can include a collection or separation container 202 that can be a container of any appropriate type. For example, the container 202 can be similar to the centrifuge or collection container disclosed in U.S. Pat. Nos. 7,179,391; 7,374,678; 7,832,566; 7,845,499; or 8,567,609; all of which are incorporated herein by reference. The container 202 can be any appropriate container operable with the buoy system 20 to affect separation of a material positioned therein. Accordingly, the container 202 can be a container known to those skilled in the art. Briefly, the container 202 can include a bottom wall 204, a side wall, such as a cylindrical side wall 206, and a top wall 208. Each of the walls 204-208 can be formed as a single portion or can be interconnected to form the separation container 202. For example, as illustrated in FIG. 4A, the top wall 208 can be included in a cap that is separable from the side wall 206.

The top wall 208 can include an introduction or first passage or valve 210 and a second withdrawal passage or valve 212. In selected configurations, such as a cap 214 can be provided to cap either or both of the passages 210 and 212. The ports 212 and 214 allow for introduction and/or withdrawal of material from the container 202.

Generally, a whole material, such as any appropriate material including whole blood, can be introduced into the separation container 202. The whole material 220 can be introduced through the introduction passage 210 into the volume of the container 202. The buoy system 20 can be initially positioned in the appropriate location within the separation container 202, such as near the bottom wall 204. Further, the introduction system that introduces the whole material 220 can be any appropriate system such as a syringe 222 that includes a plunger 224 that can be pushed in the direction of an arrow 226 to deliver the material to within the separation container 202.

With reference to FIG. 4B, the container 202 including the whole material 220 can be subjected to a separation force, such as within a centrifuge including those generally known in the art, for example the 755VES Centrifuge system, sold by The Drucker Company having a place of business at Port Matilda, Pa. and including those described in U.S. Pat. Nos. 7,179,391; 7,374,678; 7,832,566; 7,845,499; or 8,567,609; all of which are incorporated herein by reference. After centrifugation, the whole material 220 can be separated into two or more components or fractions, such as including three fractions. Three fractions can include a first fraction 230, a second fraction 232, and a third fraction 234. During a centrifugation, the heaviest fraction 230 can move towards the bottom wall 204 if the separation container 202 is positioned within the centrifuge such that the centripetal force is towards the bottom wall 204. The second fraction 232 can be a middle density fraction and the third fraction 234 can be a substantially light fraction. Further, as illustrated in FIG. 4B, the buoy system 20 can move to a selected area between or amongst the fractions 230-234. For example, the buoy system 20 can move such that the collection volume 30 substantially collects, or is positioned at the location of, the second fraction 232.

The buoy system 20 can be designed and include a selected density such that the collection volume 30 is positioned at the level of the second fraction 232. For example, the density of the second fraction 232 can be known or selected and the buoy system 20 can be formed to include a similar density. The buoy system 20, for example, may have a density of about 1.059 grams per cubic centimeter ($g/cm^3$) to about 1.061 $g/cm^3$. Further, according to various embodiments, the second fraction 232 can have a density that is slightly greater (such as about 0.5% to about 5% greater) than the density of the buoy system 20 and include materials such as a buffy coat of whole blood. The buffy coat of whole blood can include platelets, white blood cells, and interleukin-1 receptor antagonist (IL-1RA or IRAP). IRAP is a protein generally encoded in humans.

After separation of the whole material into the selected fractions, the blocking wall 90 may be moved to allow for the opening of the passages 80 through the first buoy 22 into the volume 72. The movement may include sliding or lifting of the blocking wall. Further, the movement may include linear and/or rotational movement.

Figure 4C:
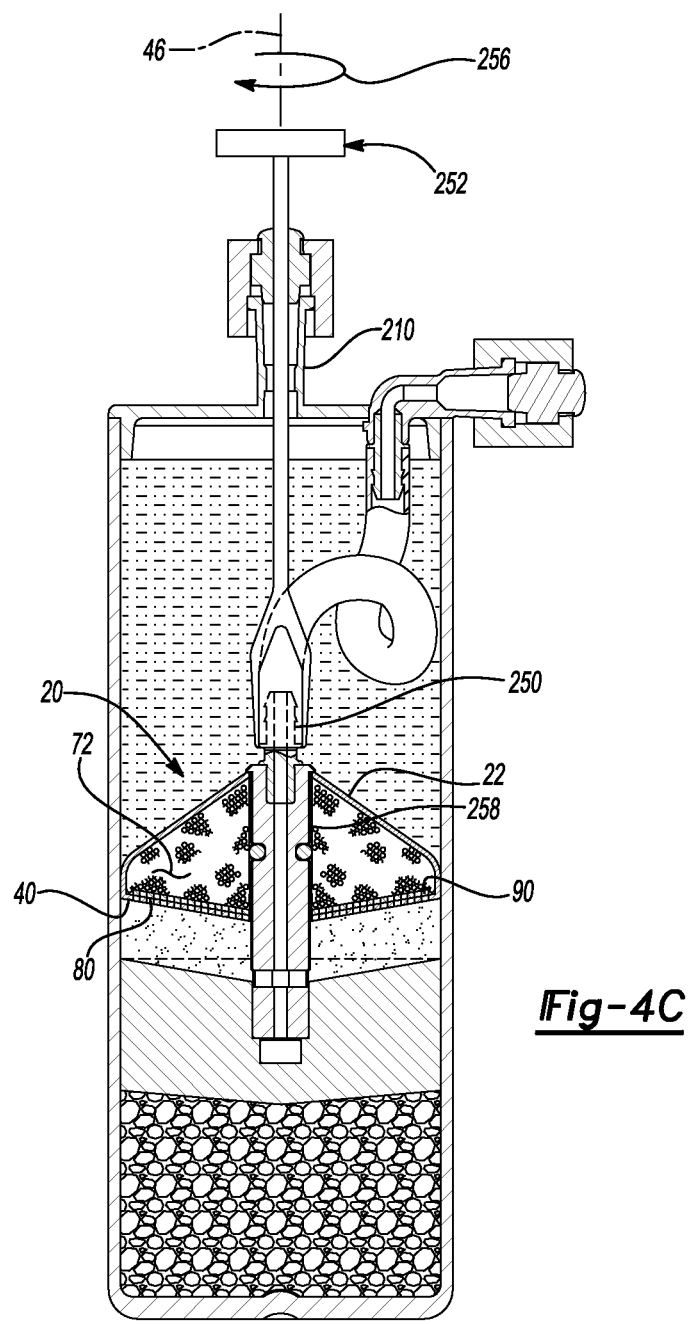
Figure 4D:
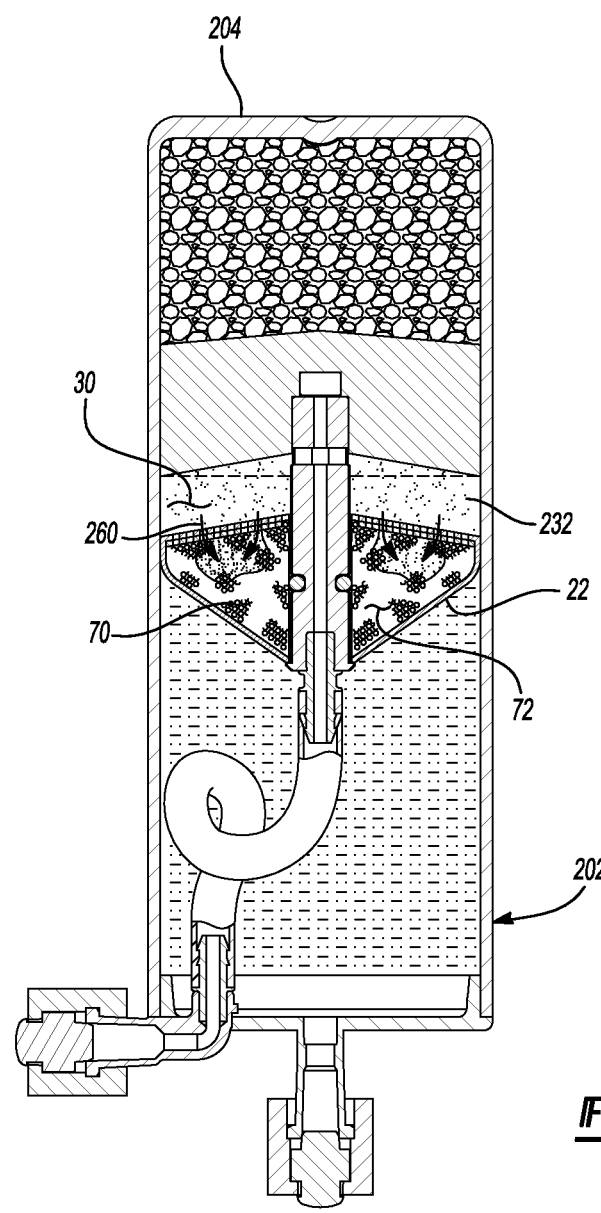
Figure 4E:
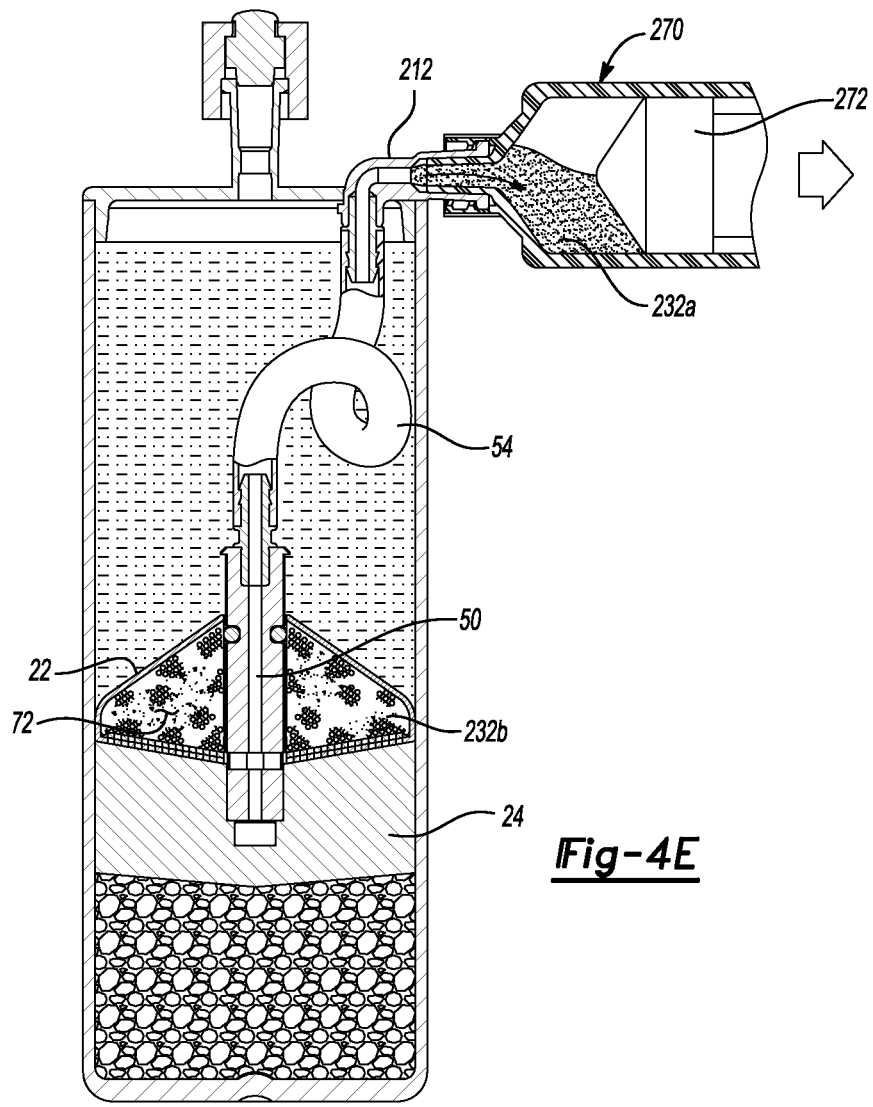

The movement of the blocking wall 90 can be performed according to various mechanisms. In various embodiments the blocking wall 90, as illustrated in FIG. 4C, may be moved by engaging a portion of the buoy assembly 20, such as near a withdrawal port 250 with a key or lever 252. The lever 252 can be passed through the port 210 to engage a portion, such as the withdrawal port 250, to rotate the blocking wall 90 around an axis 46 to allow for alignment of the blocking wall passages 92 with the wall passages 80 of the wall 40 of the first buoy member 22. For example, the lever 252 can be rotated generally in the direction of arrow 256 around the axis 46 to move the blocking wall 90 relative to the first buoy 22. In rotating the lever 252, an extension or a movable wall member 258 that can be interconnected with the withdrawal port 250 can be moved to rotate the blocking wall 90. Accordingly, the blocking wall 90 can be moved to allow opening or forming the complete passages through passages 80 into the volume 72 of the first buoy 22.

Once the blocking wall 90 has been moved to align the blocking wall passages 92 and the first wall passages 80, the container 202 can be manipulated, such as inverted, to cause the second fraction 232 to move generally in the direction of arrows 260 such that the second fraction 232 moves into the volume 72 within the first buoy 22. As the second fraction 232 moves into the volume 72, it may contact and interact with the beads 70 positioned within the volume 72 of the first buoy member 22. As discussed above, the beads 70 can be any appropriate bead, such as a glass bead, a desiccating bead, or the like. Accordingly, for example, if the beads 70 are desiccating beads, then a portion of the water or aqueous portion of the second fraction 232 can be drawn into the desiccating beads 70. This allows the second fraction 232 to be dried and concentrated to concentrate non-water portions of the second fraction 232. This may decrease an overall volume of the second fraction 232 and allow for an optimization of the withdrawal and collection of the non-water portions of the second fraction 232.

After a selected passage of time, the container 202 can be reoriented such that the bottom wall 204 is moved or positioned generally in the direction of the force of gravity to allow a desiccated or dried portion 232a of the second fraction 232 to be moved back into the collection volume 30. The desiccated fraction 232a may also be an augmented fraction, it is understood that an augmented fraction may be augmented in various manners. For example, a fraction separated from the whole material may be reacted with a chemical agent in the buoy member 22. It is understood that the container 202 can be repositioned into a centrifuge to allow for centrifugation to assist in the removal of the dried portion 232a from the desiccating beads 70 within the volume 72. According to various embodiments, after a selected period of time, removal of the dried portion 232a of the second fraction 232 from the volume 72 may occur through withdrawal by way of the withdrawal bore 50 and withdrawal tube 54 to a withdrawal syringe 270.

The withdrawal syringe 270 can interconnect with the withdrawal port 212 and a plunger 272 or other mechanism, such as a pump or vacuum, can be used to withdraw the desiccated fraction 232a into the syringe 270. A water or aqueous portion 232b can be captured or maintained in the volume 72 of the first buoy member 22 such that the withdrawn desiccated fraction 232a is substantially concentrated relative to the initial second fraction 232. The collected fraction 232a can have a higher concentration of IRAP, such as about 10,000 picograms/milliliter (pg/ml) to about 110,000 pg/ml relative to the initial second fraction 232. Further, the collected fraction 232a can have a higher concentration of IRAP, such as about 5% higher to about 1,000% higher relative to the initial second fraction 232 (including about 10,000 picograms/milliliter IRAP to about 40,000 picograms/milliliter IRAP).

Turning reference to FIGS. 5A and 5B, the buoy assembly 20 illustrated therein may include the first buoy member 22, the second buoy member 24, and the third buoy portion or connecting portion 26. The buoy assembly 20 can be substantially similar to the buoy assembly 20 discussed above and can include a volume 72 formed within the first buoy member 22. The buoy assembly 20, therefore, can also be used with a separation container 202 and any system and method as described above. The buoy assembly 20, as illustrated in FIGS. 5A and 5B, may include a blocking plate 300 rather than the blocking plate 90. The blocking pate 300 may include the blocking passages 302 that can be moved from an unaligned first position to an aligned position second position relative to the passages 80 in the first buoy member 22 through the first wall 40. The blocking plate 300 can include a configuration, such as a magnetic configuration or portion. The magnetic portion includes a south pole at a first end 310 and a north pole at a second end 312. The north and south poles can be magnetic poles and allow for an external magnet 320 to interact with the poles 310, 212 of the blocking plate 300.

For example, as illustrated specifically in FIG. 5A, the external magnet 320 can have a north pole 322 that is positioned near the south pole 310 of the blocking plate 300. Due to the magnetic interaction, exemplarily illustrated by the arrows 324, the blocking plate 300 can generally move in the direction of the arrow 326 to an unaligned or blocking orientation. The movement of the blocking plate or wall 300 may be substantially linear and transverse to the axis 46. Also, a track or groove may be formed in the buoy member 22 to guide the movement of the blocking wall 300. As discussed above, the buoy assembly 20 can then be used to assist in separation of various fractions of the whole material, including the separation of the second fraction 232 into the collection volume 30.

The buoy assembly 20 can then have an external magnet 320 oriented such that a south pole 330 is positioned near the south pole 310 of the blocking plate 300. Due to the magnetic interaction, illustrated by the arrows 332, the south pole 330 of the external magnet 320 can repel the south pole 310 of the blocking plate 300 to move the blocking plate 300 generally in the direction of arrow 334. Upon moving the blocking plate 300 the blocking plate passages 302 may be aligned with the passages 80. In this way, the collection volume 30 can be open to the internal volume 72 within the first buoy member 22, similar to the manner discussed above.

It is understood that various indicia may be used to indicate orientation of the blocking wall 300 relative to the buoy member 22. For example, the blocking wall 300 may be positioned and held in the buoy member 22 such that the south pole end 310 is near an "S" indicia on the buoy member 22. The container 202 may be clear or transparent such that the "S" may be seen through the container wall 206. Similarly the buoy member 22 may include an "N" indicia near the north pole 312 of the blocking wall 300. The external magnet 320 may also include a "N" indicia near the north pole end 322 and a "S" near the south pole end 330. Thus, a user will be able to read the indicia and determine the appropriate end of the external magnet 320 to place near the selected end of the blocking wall 300 to move the blocking wall 300 in the selected direction. The blocking wall 300, for example, may be rotationally fixed relative to the axis 46 but able to slide transversally relative thereto.

Accordingly, the external magnet 320 can be oriented relative to the blocking plate 300 positioned within the or relative to the first buoy member 22 to move the blocking plate 300. By moving the blocking plate 300, the blocking plate passages 302 can be selectively aligned or unaligned with the passages 80 through the first surface 40 of the first buoy member 22. As discussed above, this can allow for access to the internal volume 72 within the first buoy member 22 to allow a material to interact with the reactant in the volume 72, such as the beads or material positioned within the volume 72. Thus, the material positioned within the collection volume 30 can be moved or allowed to access the volume 72 within the first buoy member 22 by passing through aligned passages and a blocking plate with the passages 80 in the first buoy member.

According to various embodiments, the beads 70 positioned within the volume 72 can include polyacrylamide beads. The polyacrylamide beads can be used to desiccate or remove water from the second fraction 232 positioned within the collection volume 30 and moved into the volume 72 within the first buoy member 22. The fraction 232, as discussed above, can include a buffy coat fraction of whole blood. Further, the second fraction 232 can include a fraction including various components of bone marrow aspirate, adipose tissue, and the like. Generally, the desiccation of the second fraction 232 can concentrate and/or release free IRAP. The IRAP can be released and or concentrated with the desiccation of the second fraction 232. Accordingly, once the desiccated fraction 232a is removed from the first buoy member 22, as discussed above, and withdrawn from the collection container 202, the concentrated IRAP can be removed and used for various procedures, such as those generally known in the art.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for separation of a selected component of a multiple component material, comprising:
    a container having a container top wall and a container bottom wall with a container side wall connecting the container top wall and the container bottom wall to define a container volume;
    a buoy system movably positioned within the container, the buoy system having:
        a first buoy member having a buoy top wall and a buoy bottom wall, the first buoy member defining a first buoy open volume;
        a second buoy member;
        a selected reactant placed within the first buoy open volume;
        a first wall passage defined through the buoy bottom wall of the first buoy member to the first buoy open volume; and
        a third buoy member that interconnects the first buoy member and the second buoy member and positioned within the collection volume;
        wherein the buoy system defines a central bore extending from the buoy top wall to an access bore on the third buoy member, wherein the central bore is fluidly isolated from the first buoy open volume;
    wherein the first buoy member movably engages the container side wall to divide the container volume into a top volume above the buoy top wall and a collection volume below the bottom buoy wall, wherein the first wall passage is oriented on the buoy bottom wall to fluidly connect the collection volume and the first buoy open volume to selectively permit the selected component to move between the collection volume and the first buoy open volume to react with the selected reactant placed within the first buoy open volume.

2. The system of claim 1, wherein the selected reactant includes a desiccating bead.

3. The system of claim 1, further comprising:
    a blocking wall; and
    a blocking wall passage;
    wherein the blocking wall is configured to be moved between a blocking configuration and an open configuration;
    wherein the blocking wall includes a magnetic portion configured to be acted upon by an external magnetic member to move the blocking wall relative to the first buoy member.

4. The system of claim 1, further comprising:
    a blocking wall;
    a blocking wall passage; and
    a lever member extending from the container, wherein the lever member is configured to move the blocking wall relative to the first buoy member between a blocking configuration and an open configuration.

5. The system of claim 1, wherein the first buoy member is configured to move relative to the second buoy member.

6. The system of claim 3, wherein the blocking wall includes solid portions configured to be aligned with the first buoy passage to block movement of any portion of the multiple component material and the first buoy member.

7. A system for separation of a selected component of a multiple component material, comprising:
- a container having a container top wall and a container bottom wall with a container side wall connecting the container top wall and the container bottom wall to define a container volume;
- a buoy system movably positioned within the container, the buoy system having:
  - a first buoy member having a buoy top wall and a buoy bottom wall, the first buoy member defining a first buoy open volume;
  - a selected reactant placed within the first buoy open volume;
  - a first wall passage defined through the buoy bottom wall of the first buoy member to the first buoy open volume and configured to be opened and closed;
  - a second buoy member; and
  - a third buoy member positioned within the collection volume and interconnecting the first buoy member and the second buoy member;
  - wherein the buoy system defines a central bore extending from the buoy top wall to an access bore on the third buoy member, wherein the central bore is fluidly isolated from the first buoy open volume;
- wherein the first buoy member and the second buoy member movably engage the container side wall to divide the container volume into at least a top volume above the buoy top wall and a collection volume between the first buoy member and the second buoy member, wherein the first wall passage oriented on the buoy bottom wall to fluidly connect the collection volume and the first buoy open volume such that the first wail passage, when opened, permits at least a first portion of the multiple component material to move between the collection volume and the first buoy open volume to react with the selected reactant within the first buoy open volume.

8. The system of claim 7, wherein the first buoy passage is formed through the bottom buoy wall of the first buoy member;
- wherein the collection volume is defined between the buoy bottom wall and the first buoy member and at least a second top wall of the second buoy member.

9. The system of claim 8, further comprising:
- a blocking wall; and
- a blocking wall passage;
- wherein the blocking wall is configured to slide relative to the first buoy member;
- wherein the blocking wall is configured to be moved from a blocking configuration to an open configuration.

10. The system of claim 9, further comprising:
- an external magnetic member;
- wherein the external magnetic member is configured to interact with the blocking wall to move the blocking wall relative to the first buoy member.

11. The system of claim 7, further comprising:
- a blocking wall; and
- a blocking wall passage;
- wherein the blocking wall is configured to be moved from a blocking configuration to an open configuration;
- wherein the blocking wail rotates around the third buoy member.

12. The system of claim 7, wherein the buoy system has a density to be positioned in a separation of the multiple component material such that the selected component is in the collection volume between the first buoy member and the second buoy member following a separation of the multiple component material.

13. The system of claim 7, further comprising:
- an introduction passage configured to allow the multiple component material into the container; and
- a withdrawal passage configured to allow the selected component to be withdrawn from the container.

* * * * *

UNITED STATES PATENT AND TRADEMARK OFFICE
CERTIFICATE OF CORRECTION

PATENT NO. : 9,937,445 B2
APPLICATION NO. : 14/269655
DATED : April 10, 2018
INVENTOR(S) : King et al.

Page 1 of 1

It is certified that error appears in the above-identified patent and that said Letters Patent is hereby corrected as shown below:

In the Claims

In Column 9, Line 33, in Claim 7, delete "wail" and insert --wall-- therefor

In Column 10, Line 24, in Claim 11, delete "wail" and insert --wall-- therefor

Signed and Sealed this
Second Day of April, 2019

Andrei Iancu
*Director of the United States Patent and Trademark Office*